(12) United States Patent
Ratner

(10) Patent No.: US 6,854,334 B2
(45) Date of Patent: *Feb. 15, 2005

(54) NEGATIVE INSPIRATORY FORCE MANOMETER APPARATUS

(75) Inventor: Jeffrey B. Ratner, Pinellas Park, FL (US)

(73) Assignee: Mercury Enterprises, Inc., Clearwater, FL (US)

(*) Notice: Subject to any disclaimer, the term of this patent is extended or adjusted under 35 U.S.C. 154(b) by 14 days.

This patent is subject to a terminal disclaimer.

(21) Appl. No.: 10/352,509

(22) Filed: Jan. 28, 2003

(65) Prior Publication Data

US 2004/0144179 A1 Jul. 29, 2004

(51) Int. Cl.⁷ .................................................. A61B 5/00
(52) U.S. Cl. ........................................... 73/700; 600/532
(58) Field of Search ................... 73/700, 715; 600/532; 128/205.23

(56) References Cited

U.S. PATENT DOCUMENTS

| | | | |
|---|---|---|---|
| 4,462,258 A | 7/1984 | Boddy | |
| 5,400,779 A | 3/1995 | De Resende | |
| 5,557,049 A * | 9/1996 | Ratner | 73/715 |
| 5,679,884 A * | 10/1997 | Kirk | 73/23.3 |
| 5,743,257 A | 4/1998 | Koehler et al. | |
| 5,749,358 A * | 5/1998 | Good et al. | 128/205.23 |
| 5,839,436 A | 11/1998 | Fangrow, Jr. et al. | |
| 6,058,933 A * | 5/2000 | Good et al. | 128/205.13 |
| 6,123,075 A * | 9/2000 | Kirk | 128/205.13 |
| 6,206,003 B1 | 3/2001 | Burch | |
| 6,378,522 B1 * | 4/2002 | Pagan | 128/207.14 |
| 6,502,573 B1 * | 1/2003 | Ratner | 128/207.17 |
| 6,584,974 B1 * | 7/2003 | Ratner | 128/205.23 |
| 6,709,403 B1 * | 3/2004 | Ratner | 600/532 |

* cited by examiner

*Primary Examiner*—Edward Lefkowitz
*Assistant Examiner*—Andre Allen
(74) *Attorney, Agent, or Firm*—Larson & Larson, PA; Herbert W. Larson

(57) ABSTRACT

The apparatus is connected by tubing to a patient. The apparatus has a manometer on one side in communication with an entrance port conveying ambient air to the patient. A spring loaded cap is depressed to block air inspired by the patient and cause such air to move a diaphragm in the manometer so that the inspired negative air pressure of the patient can be recorded. As soon as the cap is released a spring opens the entrance port to continue normal flow of ambient air to the patient.

14 Claims, 6 Drawing Sheets

NEGATIVE INSPIRATORY FORCE MANOMETER APPARATUS

BACKGROUND OF THE INVENTION

This invention relates to manometers used in weaning a patient from a ventilation system. More particularly, it refers to a disposable manometer that monitors a patient's negative or suction air pressure output upon the manual blocking of an output port.

Manometers for measuring air pressure in a patient are well known. Removing a patient from a ventilation system is sometimes a difficult decision because a determination must be made as to whether the patient is breathing on his or her own with sufficient air pressure absent the use of the artificial ventilation system. A single patient use disposable mechanical test apparatus for determining the ability of a patient to breath on his or her own ability would be a great assistance to patient care givers. No such apparatus exists at present.

SUMMARY OF THE INVENTION

The present invention solves the problem by providing an apparatus containing a single patient use disposable manometer adapted to be connected to a patient's airway to measure maximum inspiratory pressure. The apparatus provides a mechanism for the care giver to determine and record a patient's inspiratory air pressure. The apparatus has a manometer on one side in communication with a patient port for transmitting inspiratory air to the patient. A spring loaded cap is depressed to block an entrance port for the patient's inspiratory air and creates a vacuum in the manometer which records maximum negative air pressure. In this manner a patient care giver can determine whether the patient is inhaling with sufficient negative pressure to remove the patient from the ventilation system. At the same time, if the patient is not breathing with sufficient negative pressure the patient is returned to the ventilation system. The inventive apparatus therefore provides a single patient use disposable mechanical device useful to test the patient's inspiratory air pressure.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE BEST MODE

Figure 1:
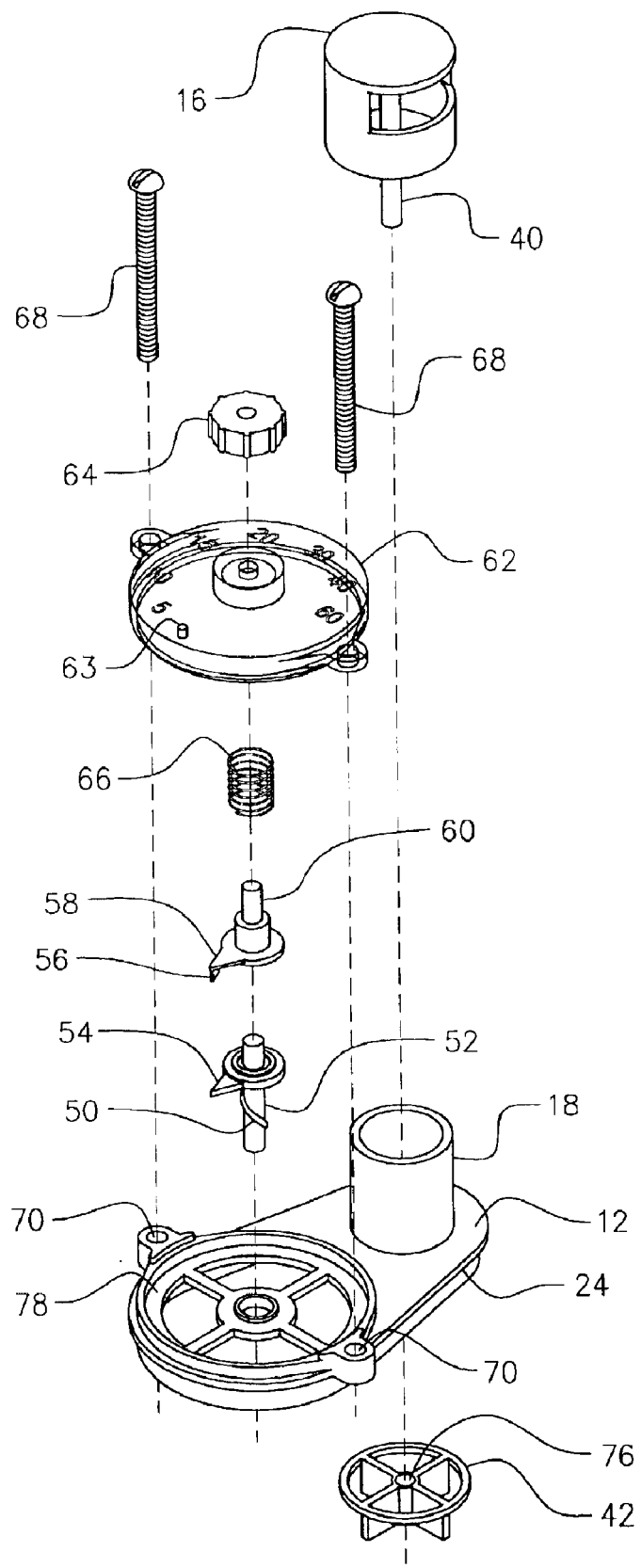
FIG. 1 is an exploded view of a top portion of the apparatus.

Throughout the following detailed description, the same reference numerals refer to the same elements in all figures.

Figure 2:
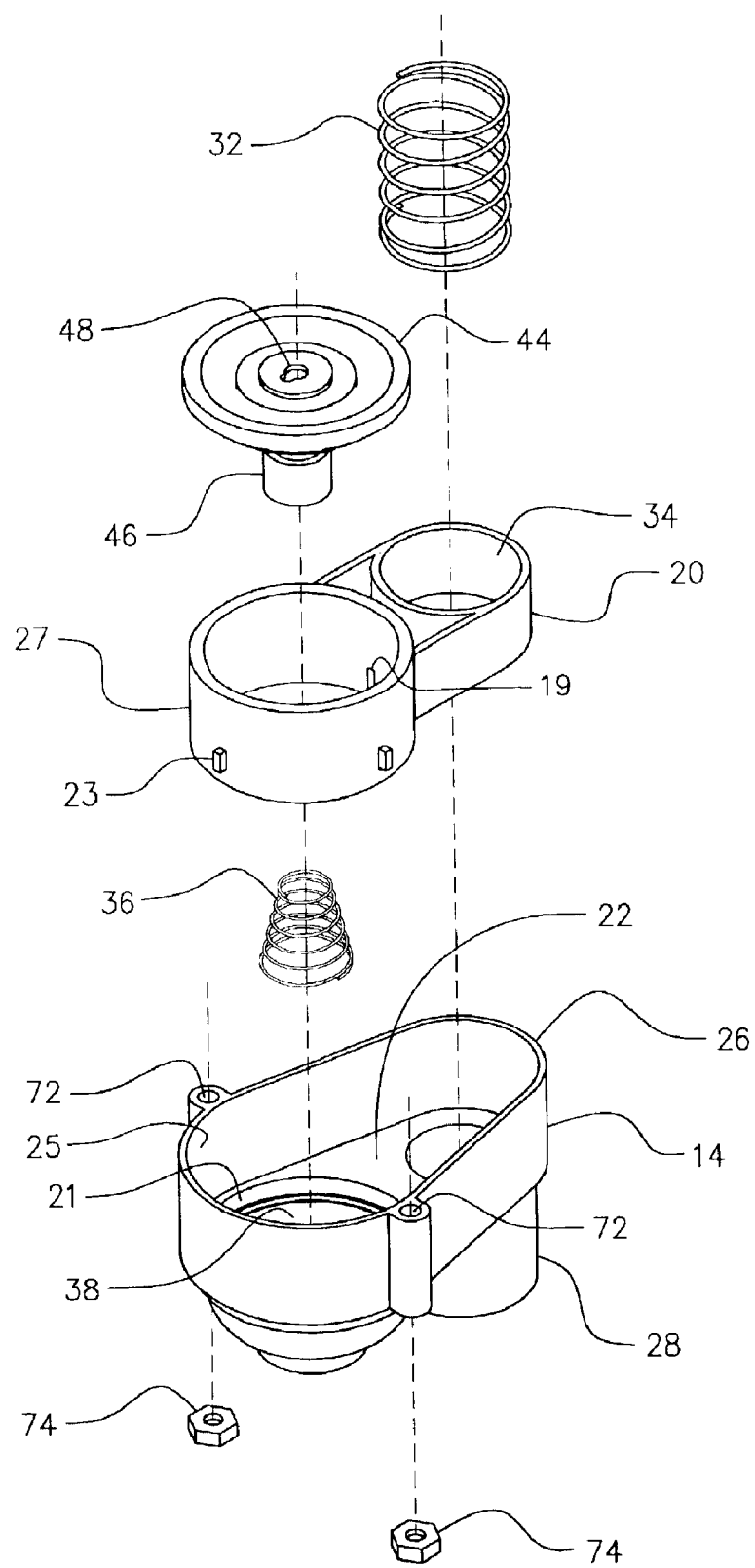
FIG. 2 is an exploded view of a bottom portion of the apparatus.
Figure 3:
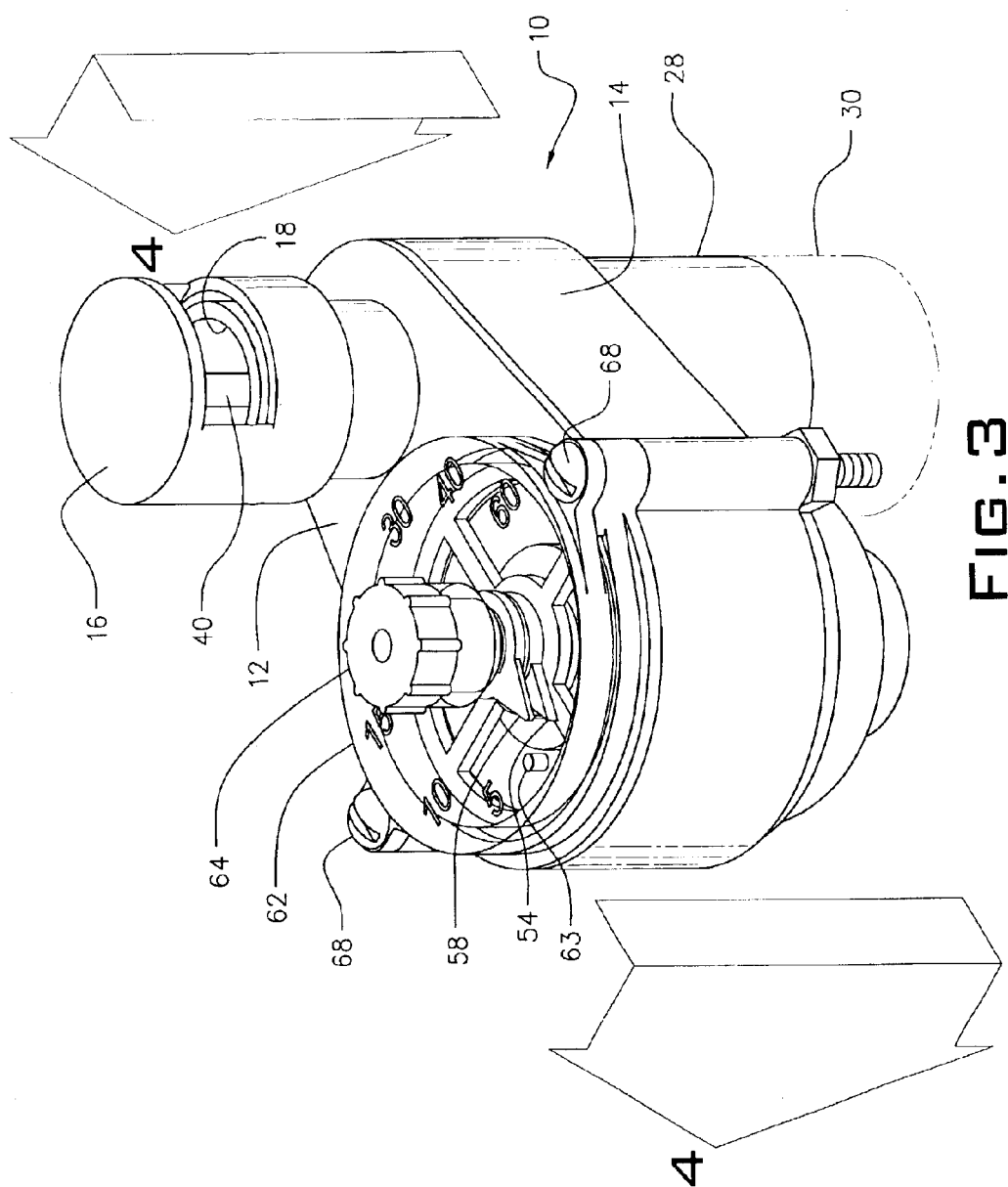
FIG. 3 is a perspective view of the apparatus.
Figure 4:
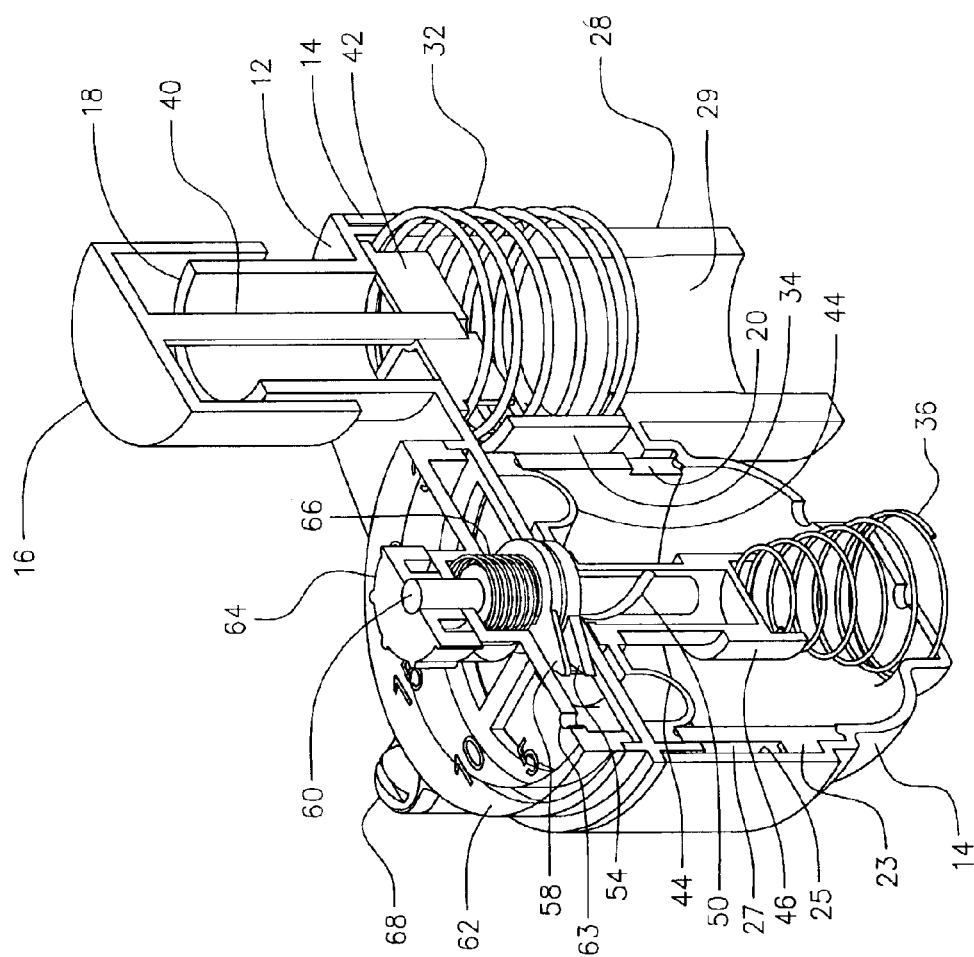
FIG. 4 is a sectional elevational view showing the manometer at rest along lines 4—4 of FIG. 3.
Figure 5:
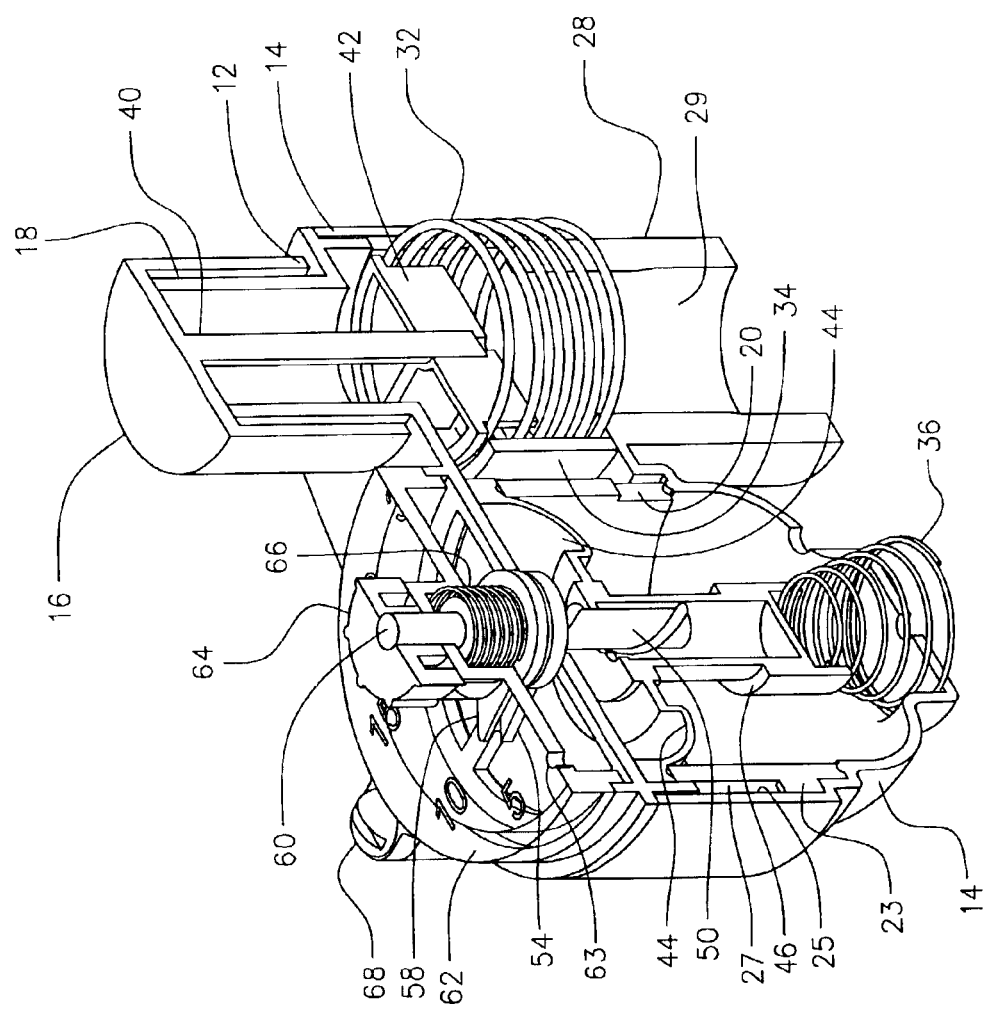
FIG. 5 is a sectional elevational view showing the manometer recording a maximum negative air pressure.

The unitary negative inspiratory force manometer apparatus shown in FIG. 3 has a top housing 12 and a bottom housing 14. A plunger cap 16 sits over an entrance port 18 on top housing 12. An intermediate housing 20 shown in FIG. 2 rests on an interior shelf 22 of bottom housing 14. Spacer tabs 23 projecting from an outside wall 27 of the intermediate housing 20 offsets from wall 25 over an annular portion 21 of interior shelf 22 as shown in FIGS. 2 and 4. A restricted orifice 19 in wall 27 allows flow of air to patient port 28. A flange 24 around top housing 12 rests on a top edge 26 of the bottom housing 14.

The patient port 28 is attached to an endotrachael tube 30. The patient's expired or inspired air passes through entrance port 18 and through channel 29 via patient port 28 when the plunger cap 16 is not depressed.

A plunger coil spring 32 is supported on shelf 22 and is surrounded by a ring portion 34 of intermediate housing 20. A conical spring 36 is positioned within receptacle 38 in shelf 22.

The plunger cap 16 has a downwardly depending spacer bar 40 attached through bore 76 to a spring depressor 42. As the plunger cap 16 is manually depressed the coil spring 32 is compressed by the force exerted on the spring depressor 42. At this point, port 18 is blocked. As soon as the plunger cap 16 is released the coil spring 32 causes the plunger cap 16 to retract and unblock the entrance port 18.

Figure 6:
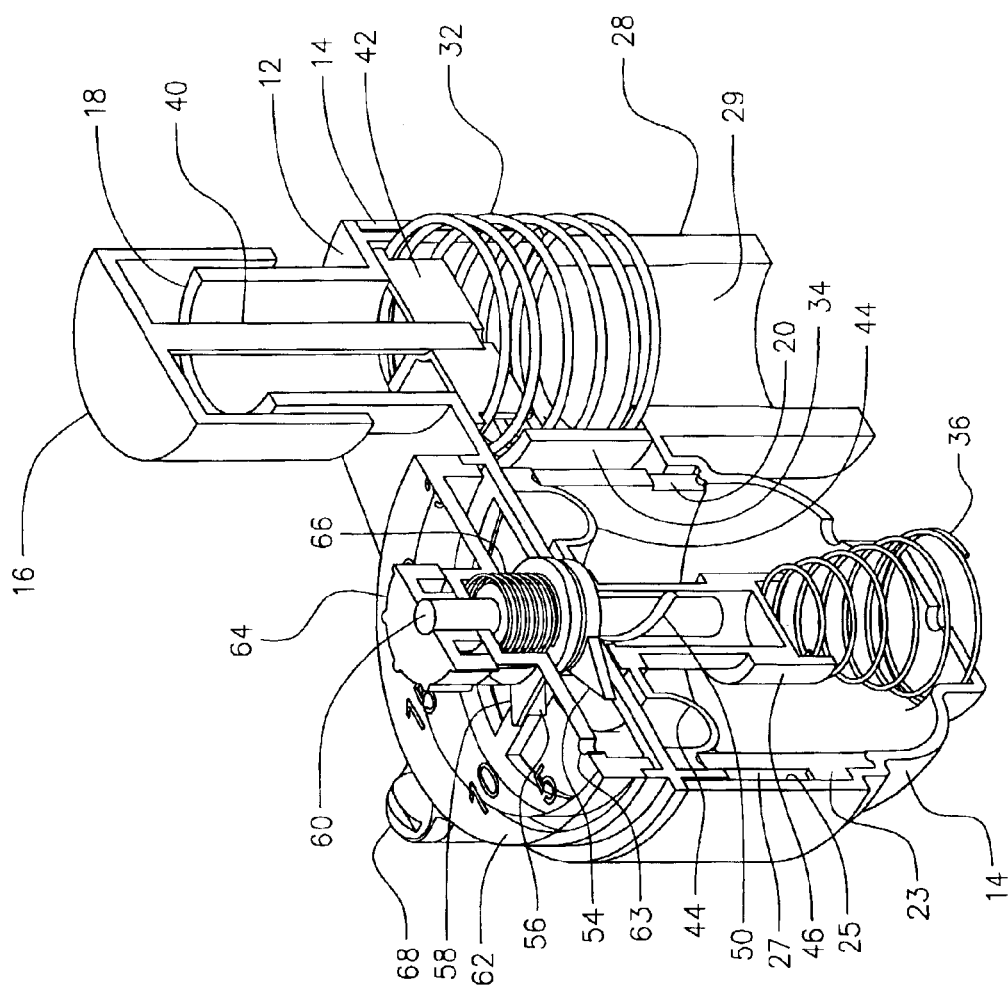
FIG. 6 is a sectional elevation view showing the manometer after negative pressure as shown in FIG. 5 is released.

The manometer side of the device 10 has an elastomeric movable diaphragm 44 movable within intermediate housing 20. Diaphragm 44 has a downwardly depending stem 46 which depresses conical spring 36 when negative air pressure from the patient port 28 causes a vacuum in the manometer of device 10 upon depression of plunger cap 16. A notch 48 in an upper portion of stem 46 receives a helix structure 50 on the exterior of shaft 52 shown in FIG. 1. Downward movement of diaphragm 44 turns shaft 52 because the helix structure 50 on the exterior wall of shaft 52 is engaged in notch 48. The turning of shaft 52 causes pointer 54 to move in a clockwise direction. Movement of pointer 54 causes engagement with flange 56 on indicator pointer 58 which also turns on second shaft 60. When patient inspiration air is no longer moving diaphragm 44, pointer 54 moves backwardly in a counter clockwise direction, but indicator pointer 58 remains at the highest point reached as shown in FIG. 6. The patient maximum negative pressure is read on the indicia printed on clear cover 62. Cover 62 has a small pinhole orifice 63 for entrance of ambient air. The entrance of ambient air above the diaphragm 44 prevents a vacuum forming above the diaphragm when the port 18 is closed. By manually turning knob 64 pointer 58 is returned to a zero position on the clear cover. Coil spring 66 keeps the pointer 58 from swinging freely.

Threaded bolts 68 pass through bores 70 on top housing 12 and bores 72 in bottom housing 14 to engage nuts 74 at a bottom portion of bottom housing 14. Alternatively, the top housing 12 and bottom housing 14 can be bonded together by glue, solvent or ultra sonically welded.

The top, intermediate and bottom housing are made from polystyrene, polycarbonate, or other polymer. The springs are made from steel, phosphor bronze or plastic and the diaphragm from an elastomer. The manometer cover 62 resting on support 78, contains numerical indicia. The cover 62 is a clear plastic such as polycarbonate so that the indicator pointer 58 and pointer 54 can be seen.

Other equivalent components can be substituted for the components employed in the apparatus 10 to have substantially the same function, in substantially the same way and create substantially the same result.

Having described the invention, what is claimed is:

1. An apparatus for measuring and recording maximum patient inspiratory air pressure, the apparatus comprising:
   a housing containing a patient port for connection to the patient and an entrance port open to ambient air;
   a manometer mounted within the housing;
   a means mounted over entry port for blocking the entrance port and causing the patient inspiratory air pressure to create a vacuum in the manometer;
   a channel within the housing connecting the patient port and entrance port for permitting flow of patient inspiratory air when the entrance port is not blocked; and
   a means for recording the patient inspiratory air pressure and viewing the said recording from outside the housing.

2. The apparatus according to claim 1 wherein the housing has a top, intermediate and bottom portion joined together, the top portion containing the entrance port and the bottom portion containing the patient port.

3. The apparatus according to claim 1 wherein the means for blocking the entrance port is a depressable cap mounted over the entrance port with a spacer bar descending downwardly from the cap through the entrance port into the channel to depress a spring, the downward depression of the cap sealing off the entrance port.

4. The apparatus according to claim 1 wherein the means for recording the patient inspiratory air pressure is a primary pointer rotating on a shaft below a clear cap over the manometer, the shaft engaged by a helix structure on an outer surface of the shaft to a notch in a stem mounted in a central portion of a diaphragm, the diaphragm converting negative air pressure from the patient on a surface of the diaphragm to rotary motion on the shaft when the entrance port is blocked.

5. The apparatus according to claim 2 wherein the top portion of the housing contains a support for a clear cover containing indicia, the support having a central aperture for passage of a rotating shaft, the shaft having a primary indicator pointer at a top portion, the intermediate portion having a right side opening promoting the flow of the patient inspiratory air and a left side opening supporting a diaphragm on a top annular edge and the bottom portion containing an interior side wall and a depression distal from the input port containing a spring, the spring depressed by a stem attached to a middle portion of the diaphragm.

6. The apparatus according to claim 5 wherein the intermediate housing portion has a restricted orifice in a side wall for passage of air.

7. An apparatus having a patient port connected to a patient, the apparatus comprising:
   a housing containing the patient port and an entrance port for flow of inspired air to the patient, and a manometer mounted within the housing for measuring and recording maximum patient inspiratory air pressure;
   a cap mounted over the entrance port so that, it can block entrance of ambient air to the patient when depressed and cause the inspired air to move a diaphragm in the manometer, a first and a second side of the apparatus adopted to be in fluid communication when the spring loaded cap is depressed; and
   the manometer containing a means for recording and viewing the maximum negative air pressure from the patient when the entrance port is blocked.

8. The apparatus according to claim 7 wherein a rod depends from the cap to a spring depressor adapted to compress a spring when the cap is depressed, the spring located within a channel, the channel in fluid communication between the patient port and the entrance port.

9. The apparatus according to claim 7 wherein the means contained within the manometer for viewing the maximum negative air pressure from the patient is a clear plastic cover containing numerical indicia, and the means for recording the maximum negative air pressure is a primary pointer rotating on a shaft below the cover, the shaft having a helix configuration on an outer surface, the helix configuration engaging a notch in a hollow stem mounted within a central portion of the diaphragm, the diaphragm converting negative air pressure on a surface of the diaphragm to rotary motion on the shaft when the cap is depressed.

10. The apparatus according to claim 9 wherein the primary pointer rotates in response to movement of the diaphragm and engages a flange on a second spring loaded indicator pointer, the primary pointer returning to zero when the negative air pressure from the patient is no longer influencing the diaphragm, the indicator pointer remaining pointed at the indicia reflecting the highest negative air pressure from the patient.

11. The apparatus according to claim 9 wherein a stem depends downwardly from the diaphragm to compress a spring when the diaphragm is in fluid communication with negative air pressure from a patient.

12. The apparatus according to claim 9 wherein the housing has a top, intermediate and bottom portion joined together by a nut and bolt.

13. The apparatus according to claim 9 wherein the top housing portion supports the clear plastic cover and contains the spring loaded cap mounted over the entrance port, the intermediate housing portion supports the diaphragm and the bottom housing portion contains the patient port on a first side and a depression on a second side containing a spring depressed by a stem depending downwardly from the diaphragm.

14. A method for determining the amount of maximum negative air pressure being inspired by a patient, the method comprising:
   providing an apparatus in communication with the patient, the apparatus having a top and bottom housing sealed together, a first side of the top and bottom housing containing a patient port and an entrance port for flow of inspired air to the patient, a second side of the top and bottom housing containing a manometer;
   providing a spring loaded cap mounted over the entrance port;
   depressing the spring loaded cap to close off an opening from the entrance port and causing patient inspiratory air to create a vacuum in the manometer on the second side of the apparatus; and
   recording the patient negative air pressure on the manometer.

* * * * *